United States Patent [19]
Kurth

[11] Patent Number: 6,004,343
[45] Date of Patent: Dec. 21, 1999

[54] UNIVERSAL PRESSURE PAD FOR FEMORAL CLAMPS

[75] Inventor: Paul A. Kurth, Rancho Palos Verdes, Calif.

[73] Assignee: The Regents of the University of California

[21] Appl. No.: 09/165,163

[22] Filed: Oct. 1, 1998

[51] Int. Cl.⁶ .................................................. A61B 17/00
[52] U.S. Cl. ....................................... 606/201; 128/122.1
[58] Field of Search ................. 606/201, 1; 128/121.1, 128/122.1, 123.1, 124.1, 125.1, 126.1

[56] References Cited

U.S. PATENT DOCUMENTS

| | | | |
|---|---|---|---|
| 4,572,182 | 2/1986 | Royse | 128/325 |
| 5,304,201 | 4/1994 | Rice | 606/201 |
| 5,931,832 | 8/1999 | Jensen | 606/1 |

*Primary Examiner*—Michael Buiz
*Assistant Examiner*—Jonathan D. Goldberg
*Attorney, Agent, or Firm*—Daniel L. Dawes

[57] ABSTRACT

A universal pressure pad for femoral clamps capable of coupling with two or more clamps of different design is provided by a generally disc-shaped pad with a central joint or boss which has a cavity with an upper spherical ball socket and a lower conical socket. Therefore, an insertion element from a clamp having a ball socket snaps into the upper ball socket cavity to form a swiveling ball and socket combination. Similarly, an insertion element from an artery clamp which has a rigid conical pin is disposed through the spherical ball socket in the upper portion of the joint and extends into the lower frustoconical section of the cavity to provide a force fit with the pin.

20 Claims, 3 Drawing Sheets

UNIVERSAL PRESSURE PAD FOR FEMORAL CLAMPS

BACKGROUND OF THE INVENTION

1. Field of the Invention

The invention relates to the field of femoral compression devices and in particular to the pressure pad which is fitted to the adjustable screw of a femoral clamp for the purpose of exerting pressure against a femoral incision in order to staunch blood flow from the puncture site.

2. Description of the Prior Art

A number of medical procedures require the puncture of a blood vessel for purposes of entry of a catheter, guide wire or needle. One such common procedure is cardiac catheterization where the femoral artery in a patient's groin area is punctured to allow passage of a long catheter through the artery into the chambers of the heart. Cardiac catheterization procedure aids in diagnosis of various heart disorders and anomalies.

Following withdrawal of the catheter, pressure must be applied to the groin area at the location of puncture in the artery to allow coagulation to take place to prevent bleeding. Several approaches to apply the necessary pressure have been followed. One approach is for a physician or nurse to manually apply pressure to the side of the puncture for an extended period of time. Another approach is to use a mechanical device to apply the pressure such as shown in Semler, "Artery Clamp," U.S. Pat. No. 3,779,249 (1973). This device, called an artery clamp, includes an upright tubular support mounted on the flat base and an arm mounted on the support in a cantilevered or perpendicular fashion to overlie the base. The arm is mounted so that it is vertically slidable along the end of the support. Mounted on the outer end of the arm is relatively inflexible, disc-shaped pressure pad formed from transparent or translucent plastic.

Before removing the catheter from the patient, the physician or nurse places the base of the clamp under the patient's thigh, and slidably positions the arm so that the pressure pad is directly over the puncture site. As the catheter is withdrawn, the arm is manually moved downward toward the base, typically through a screw adjustment, to cause the pad to compress the artery and to prevent bleeding. After blood coagulation has been established, the arm is unlocked and removed.

Another design for a femoral artery clamp is shown by Freund et al., "Adjustable Compress Apparatus," U.S. Pat. No. 4,742,825 (1988). Freund is similar to Semler in that it includes a base, a support and an arm to which a pad is adjustably positioned. The differences between Freund and Semler, for example, as with many other artery clamp designs is in the connection of these various elements to each other and their adjustability.

Another example of an adjustable pressure tourniquet using a screw adjustment with a pad is shown in Plummer, "Tourniquet," U.S. Pat. No. 1,281,653 (1918) in which a screw adjustment on a flexible belt tourniquet is mounted on its lower end with a ball joint fit into expandable socket of a disc-shaped hard pad.

The number of examples of artery clamps or tourniquets using adjustable means to bring a pad to bear against a puncture site could be multiplied even further. A number of different designs are available in the market and among their various other differences, the exact shape and nature of the fitting between the titration or adjustable screw and the pressure pad varies. As a consequence, it is necessary for medical practitioners to stock separate pads for each different type of arterial clamp which may be used or available in their hospital or clinic. The construction details of the fitting between the titration screw and the pad varies from manufacturer to manufacturer and there is no universal standard.

Therefore, what is needed is some type of design by which the need for inventorying multiple types of pads may be avoided.

BRIEF SUMMARY OF THE INVENTION

The invention is a pad for use in applying pressure to puncture site on a patient adapted for coupling to a clamp of a first and section design. The pad comprises a disc shaped portion having a peripheral edge, a puncture site contacting side and an opposite side to the puncture site contacting side. A joint is disposed on the opposite side of the disc shaped portion. The joint has a cavity defined therein with a longitudinal axis and a first and second longitudinal section of the cavity. The first section is distal from the puncture site contacting side and the second section is proximate to the puncture site contacting side. The first section of the cavity generally has an internal surface which is an azimuthal section of a spherical surface and thereby forms part of a releasable ball and socket combination permitting coupling to the clamp of the first design and permitting movement of the pad relative to the patient for self-adjustment of to the pad and to conform with the contour of the puncture site. The second section of the cavity has an internal frustoconical surface and thereby forming part of a releasable pin and socket combination permitting coupling to the clamp of the second design.

The first section of the joint includes a circumferential bevel defined in the first section as an entry aperture to the cavity to permit swiveling of the pad above the joint. The pin of the pin and socket combination is frustoconical in shape and the second section of the joint has a length of the frustoconical cavity extending to a diameter less than the frustoconical pin to be inserted therein. The second section of the joint may have a length of the frustoconical cavity extending to a diameter less than the frustoconical pin to be inserted therein. when the pad is used in the combination with a frustoconical pin of the clamp.

The pin has an engagement surface with a predetermined longitudinal length and the second section of the joint has a longitudinal length which is as long as the predetermined length of the engagement surface of the pin. The azimuthal spherical surface of the cavity is at least that portion of the spherical surface from the equator to an upper latitude.

The pad may further comprise a rectangular slot radially defined within the peripheral edge. The pad has a center and the rectangular slot has an inner edge defined at a predetermined distance from the center of the pad. The contacting side of the pad is sloped away from the puncture site from the proximity of the center of the pad to the inner edge of the rectangular slot. The pad may further comprises a plurality of stiffening ribs extending from the joint outwardly to the periphery. The peripheral edge has rounded smooth contours disposed toward the puncture site.

The invention is alternatively defined as a pad for use in applying pressure to a puncture site of a patient by a clamp comprising a pressure plate having a peripheral edge, a contacting surface for applying pressure to the puncture site and a surface opposing the contact surface. An universal joint is provided and adapted to be temporarily coupled to at least two different types of insertion elements. The universal joint fits either of the two insertion elements without any required adjustment of the pad.

The universal joint temporarily couples to either an insertion element capable of swiveling or to a fixed insertion element incapable of swiveling. The insertion element capable of swiveling comprises a ball and socket combination. The insertion element not capable of swiveling comprises a forced-fit pin and socket combination. The force-fit pin is a frustoconical shaped pin. The universal joint is comprised of rigid material having a predetermined amount of resiliency so that the insertion elements are temporarily coupled to the pad by compression of the universal joint about the insertion element.

The invention now having been briefly summarized can be better visualized by turning to the drawings wherein like elements are referenced by like numerals.

The invention now having been illustrated in the foregoing drawings, its various details and embodiments can be better understood by turning to the following detailed description.

DETAILED DESCRIPTION OF PREFERRED EMBODIMENTS

A universal pressure pad for femoral clamps capable of coupling with two or more clamps of different design is provided by a generally disc-shaped pad with a central joint or boss which has a cavity with an upper spherical ball socket and a lower conical socket. Therefore, an insertion element from a clamp having a ball socket snaps into the upper ball socket cavity to form a swiveling ball and socket combination. Similarly, an insertion element from an artery clamp which has a rigid conical pin is disposed through the spherical ball socket in the upper portion of the joint and extends into the lower frustoconical section of the cavity to provide a force fit with the pin.

Figure 1:
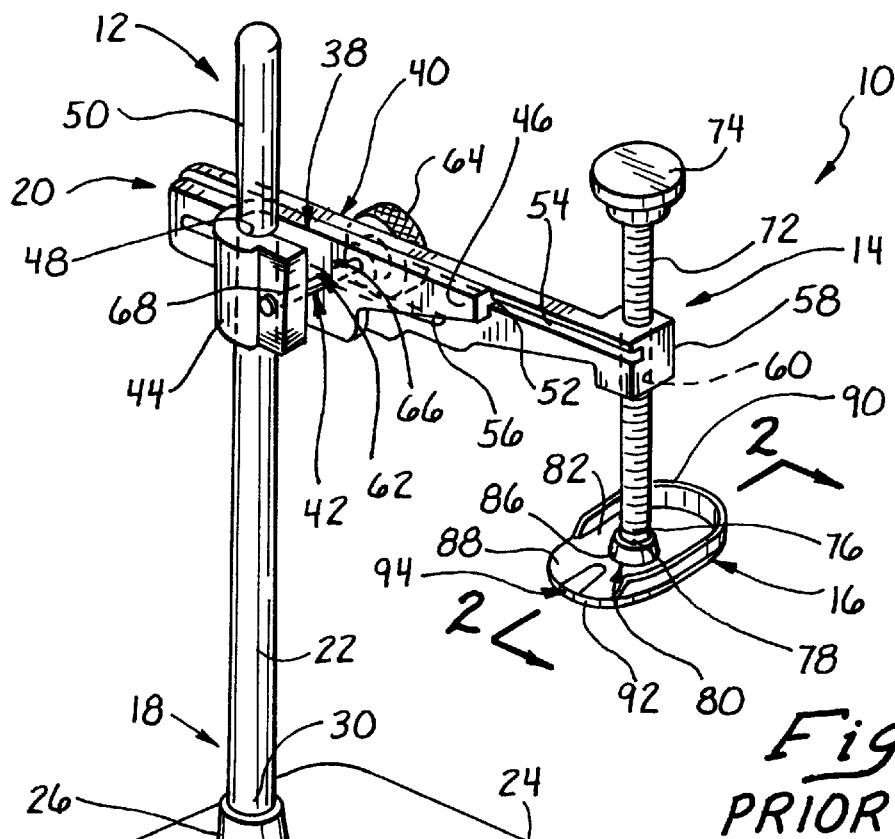
FIG. 1 is a prospective view of a femoral artery clamp as currently utilized in the medical profession using one type of pad fitting.

Before considering the design of the present invention, consider first femoral clamp 10 as shown in prospective view in FIG. 1 as the whole in order to understand the context in which the pad of the invention is used. Adjustable femoral clamp 10 includes an adjustable stand 12, pressure adjustment mechanism 14, and a pressure pad 16. The parts of adjustable stand 12 are fabricated from aluminum. The pressure adjustment mechanism 14 is made out of stainless steel and pressure pad 16 from transparent polyethylene. However, other materials may be substituted according to their similar characteristics.

Adjustable stand 12 includes a support frame 18 and a patient-size adjustment mechanism 20. Support frame 18 has a support post 22 fabricated from rigid material and a flat base plate 24 with a support block 26 fixed on the upper side of plate 24. Support block 26 has a recess sized to snugly receive an end 30 of support post 22, thereby mounting the post in an upright configuration relative to base plate 24. Flat base plate 24 is adapted to be inserted under the patient and left on a surface which supports the patient.

Mechanism 20 includes a clamp 38, an arm 40 and a releasable lock 42. Clamp 38 has a J-shaped configuration, a curved mounting portion 44 and a straight guiding portion 46. Portion 44 defines a general cylindrical passage 48. The upper end portion 50 of post 22 extends through passage 48 whereby it mounts clamp 38 thereon above base plate 24 to allow for sliding movement in a generally vertical direction along support post 22 toward and away from base plate 24. Mechanism 20 may also pivot azimuthally around post 22. When clamp 38 is mounted on post 22, its straight guiding portion 46 extends generally horizontally in a perpendicular transverse direction relative to post 22. Portion 46 of clamp 38 has a linear guide rail 52 formed on it which protrudes outwardly from the side of clamp 38 opposite the support post 22. Guide rail 52 extends longitudinally along the straight portion 46 of clamp 38 and is generally parallel to base plate 24.

Arm 40 of mechanism 20 is longer than clamp 38 and has a longitudinal groove 54 defined in it with a cross sectional size adapted to receive guide rail 52 of clamp 38. Arm 40 is thereby mounted on clamp 38 for sliding movement in a generally horizontal direction transverse to post 22 and is generally parallel to base plate 24. A slot 56 is defined through arm 40 and is generally parallel to and below groove 54. Stem 62 extends through slot 56 and allows arm 40 to be extended horizontally toward or away from post 22. Arm 40 has an outer end the form of an enlarge square-shaped block 58 which has an internally threaded opening 60 formed vertically through block 58.

Releasable lock 42 of mechanism 20 is used to fasten clamp 38 in any selective vertical position along post 22 and any pivotally adjustable position around post 22. At the same time, it is used to fasten arm 40 at a selected horizontal position along clamp 38. Thus the clamp and arm in the size of the adjustable stand 12 can be adjusted for locating block 58 in the outer end of arm 40 above and in a desired position relative to the puncture site in a patient whose groin has been positioned between arm 40 and base plate 24 with a patient's hip along side support post 22.

Specifically, lock 42 takes the form of an elongated threaded stem 62 having a knob 64 attached to that one end. Stem 62 extends through slot 56 and arm 40 and clearance hole 66 in straight portion 46 of clamp 38 and at its opposite end is threaded through an eternally threaded hole 68 tapped in the outer end of portion 44 of clamp 38 in alignment with clearance hole 66. Clamp 38 is clamped to post 22 and arm 40 is secured to clamp 38 by screwing stem 62 into hole 68 until knob 64 is tightened down against the outer surface of the arm. Then by loosening knob 64, the position of arm 40 can be horizontally slid along clamp 38. At the same time the position of clamp 38 can be vertically slid along post 22 and adjusted into position about the periphery of post 22.

Pressure mechanism 14 includes an elongated member in the form of a titration screw or threaded shaft 72 threadably mounted through an opening 60 in block 58 at the outer end of arm 40. Shaft 72 has a knob 74 attached to its upper end and an inwardly tapered section 76 defined in its lower end which is provided with a spherical ball 78 as best shown in cross-sectional view in FIG. 2. Ball 78 forms part of a ball and socket joint generally denoted by reference numeral 80 in FIG. 2. By turning knob 74 shaft 72 can be vertically moved relative to arm 40 toward away from base plate 24 and thus toward or away from the puncture site in the groin of a patient positioned between base plate 24 and arm 40. In this manner the pressure pad 16 mounted on the lower end of shaft 72 provides a pressurized contact with the patient in the area of the puncture site.

It must be understood that pad 16 of apparatus 10 includes a generally flat disc-shaped portion 82. The disc shape portion is intended to include many different shapes having a curved periphery such as circular, oval, elliptical shapes and free-form shapes. In addition, portion 82 may be textured on a lower side 84 to engage the patient's skin so that pad 16 does not rotate when threaded shaft 72 is turned against pressure applied by pad 16. A socket 86, which is part of the ball and socket joint 80, is attached to or integrally formed with pad portion 82 and is centrally located on its upper opposite side 88. Socket 86 of pressure pad 16 releaseably mates with ball 78 on shaft 72 to allow for generally pivotal movement of pad 16 relative to pad shaft 72. The range of the movement is limited by tapered section 76 and the lower end of shaft 72.

Figure 3:
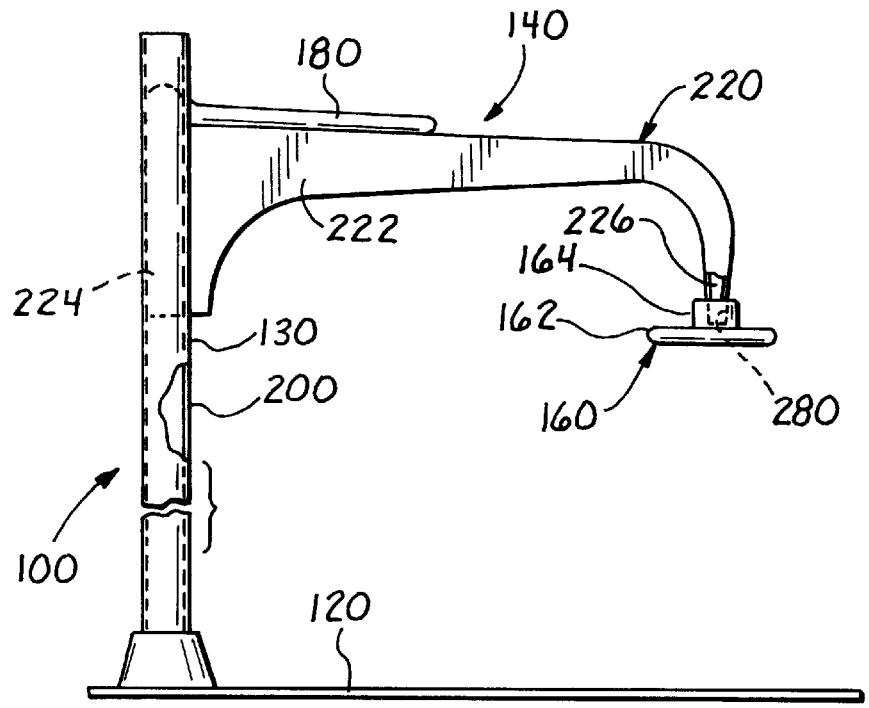
FIG. 3 is an enlarged cross-sectional view of the screw-to-pad fitting utilized in a type of arterial clamp currently in use within the medical profession.

The foregoing details have been provided as an example of the context in which the pad of the invention is used and should not be understood or read as limiting the invention. For example, a second type of an arterial clamp 100 is shown in side elevational view in FIG. 3. Again, clamp 100 includes a base 120, an elongated support 130 perpendicular to base 120 and an elongate arm 140 generally perpendicular transverse to support 130 and parallel to base 120. Arm 140 is slideably mounted on support 130 and a pressure pad 160 is carried on arm 140. Clamp 100 also includes a releasing lever 180 described below. In the configuration shown in FIG. 3 arm 140 is locked against movement on support 130 with base 120 and pressure pad 160 is in contact with and bears against opposite sides of the patient's thigh. Support 130 is disposed with its longitudinal axis substantially normal to the base 120 and assumes the form of a hollow, square cross-sectional tube having an elongated slot 200 extending substantially along its right side as shown in FIG. 3. Arm 140 includes a portion 220 in a friction block (not shown) mounted on arm 220. Arm 220 includes an elongated somewhat shallow inverted U-shaped outer part 222 which extends integrally from an inner part 224. Although not illustrated in FIG. 3, part 224 is elongated and has a generally square cross-sectional configuration which is slightly smaller in the cross-sectional area of the interior support 130. Portion 224 is slideably received in the interior of support 130 with outer part 222 extending through slot 200 and over base 120. The outer down turned end 226 of outer portion 222 is formed with a conical outside surface. Pressure pad 160 includes a generally disc-shaped base 162 on top of which is formed an integral mounting boss 164. Boss 164 is provided with a conical socket 280 which matches with and receives end 226 in arm 220. Pad 160 is detachably held by friction on arm 220. Pad 16 is formed of a suitable transparent plastic such as polycarbonate resin made by General Electric under the tradename Lexan. Arm 220 is adjusted vertically until the appropriate height is obtained and then lever 180 pulled upward to force the frictional member (not shown) to lock arm 220 in place. Downward pressure is provided through arm 220 prior to locking when it is manually adjusted over the puncture site.

Figure 2:
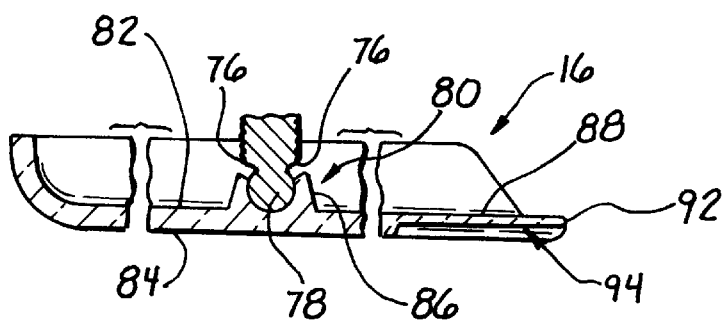
FIG. 2 is an enlarged cross-sectional view of the screw-to-pad fitting for the clamp of FIG. 1 in which a ball joint connection is employed.

Again, FIG. 3 has been shown only for the purposes of context and for showing another commonly used femoral clamp with a distinctly different arm-to-pad fitting, which is incompatible with a ball and joint socket 80 shown in FIG. 2. Pads which fit clamp 10 of FIG. 1 do not fit clamp 100 of FIG. 3. Medical practitioners use both of these types of artery clamps and are thus required to maintain separate inventories of pads 16 and 160 to fit the corresponding clamp 10 or 100.

Figure 4:
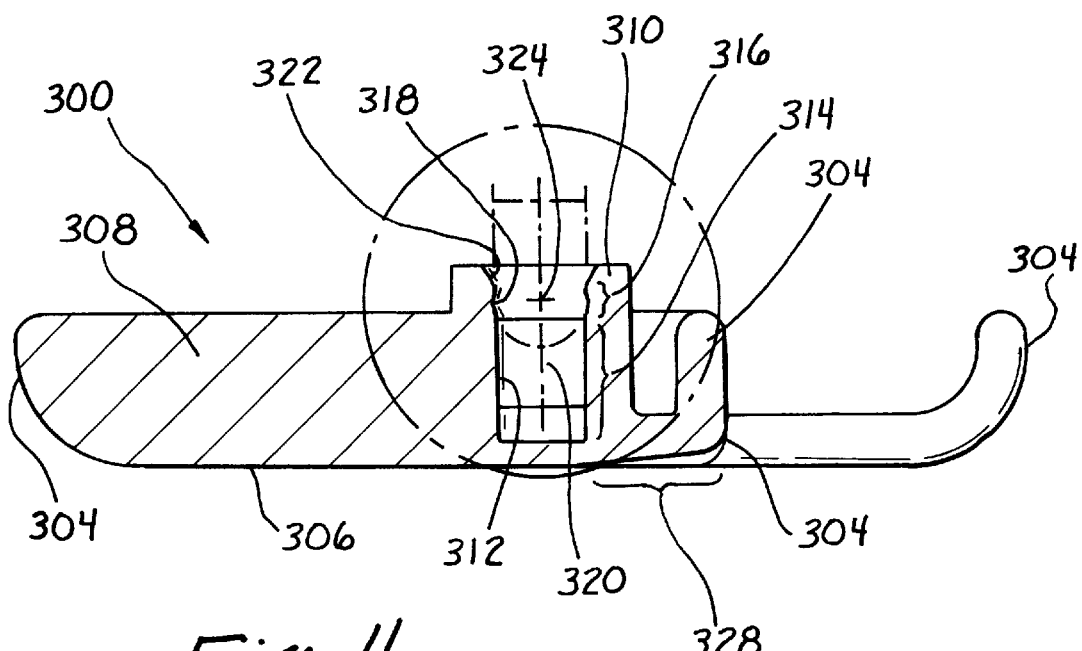
FIG. 4 is a cross-sectional view of the invention wherein a universal pad capable of fitting with the arterial clamps of designs of both FIGS. 1 and 3 may be employed.
Figure 5:
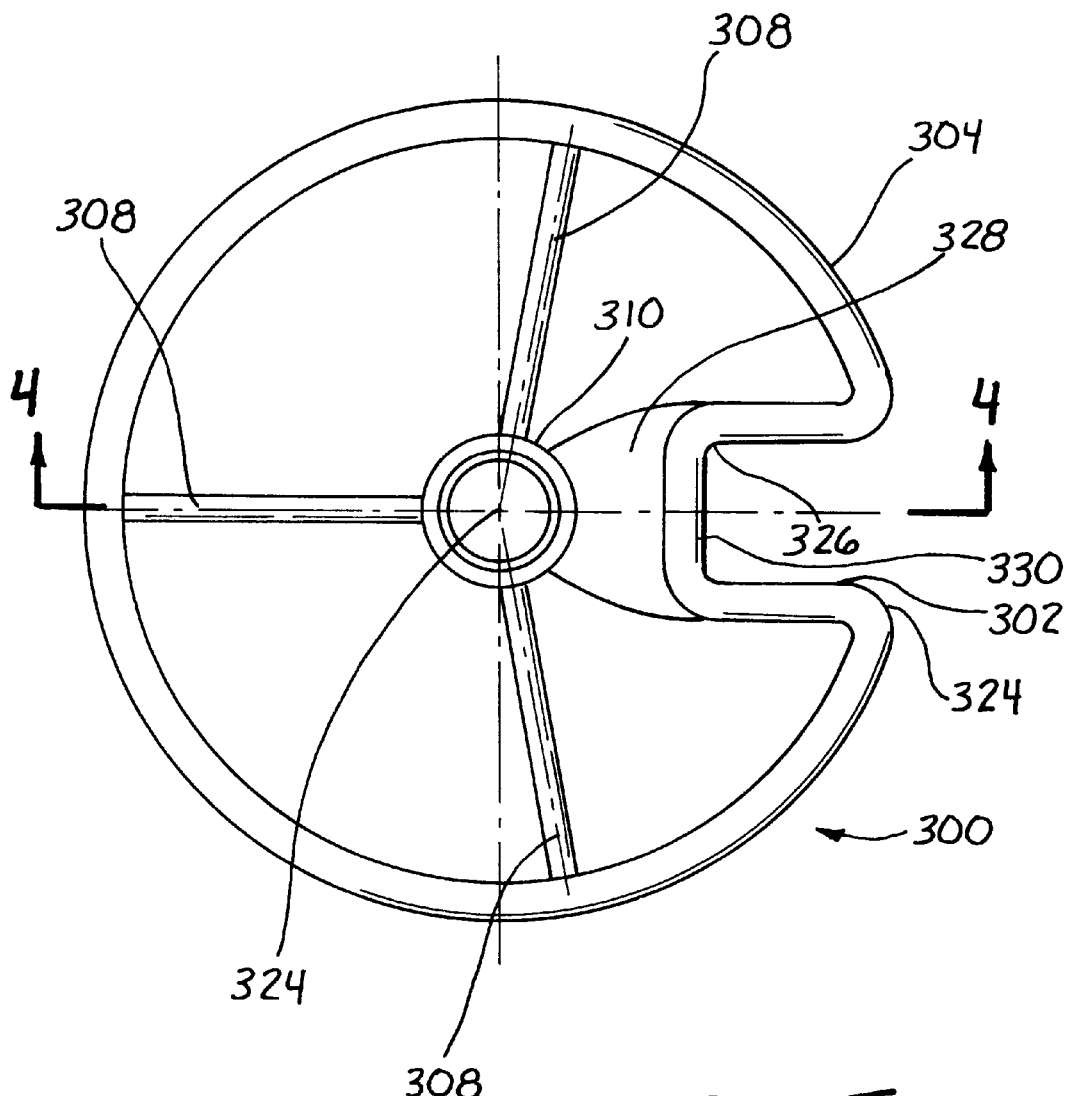
FIG. 5 is a top elevational view of the pad of FIG. 4.

According to FIG. 4, a disc, generally identified by reference numeral 300, is illustrated in cross-sectional view along a diameter line 44 as seen in the top elevational view of FIG. 5. Pad 300 may have any shape or form known in the art or later discovered and is shown for the purposes of illustration as a generally circular disc in which a rectangular indentation 302 has been formed. Pad 300 may be made of any material known in the art or as may later be determined although translucent plastic is the currently favored material in the art. As shown best in the cross-sectional view of FIG. 4, pad 300 includes smooth rounded edges 304 which curve to lower surface 306 which in turn is brought to bear against the puncture site. In this manner there is no sharp cutting edge or concentrated pressure points defined by pad 300 against the pressure site. Instead, the pressure is smoothly spread across puncture site with smooth gradations by rounded edges 304.

In the illustrated embodiment pad 300 as shown in the top elevational view of FIG. 5 also includes radial reinforcing ribs 308 to provide additional structural rigidity to pad 300, particularly in the case where pad 300 is made of a softer or more flexible plastic.

Pad 300 has a joint 310 centrally positioned in the disc shape. Joint 310 has a truncated conical lower cavity surface 312 defined in its lower portion 314 of cavity 320 and a partially spherical socket surface 318 defined within an upper portion 316 of cavity 320. Socket surface 318 thus forms a partial azimuthal section of a spherical surface having a radius of curvature which accepts ball 78 of a clamp with the design of clamp 10 of FIG. 1. A bevel 322 is provided at the entry of cavity 320 above socket surface 318 to accommodate limited rotation of pad 16 about center 324 in all directions. Frustoconical surface 312 in lower portion 314 of cavity 320 similarly has a friction-fitting surface similar or identical to socket 280 to couple to a clamp of the design of clamp 100 in FIG. 3.

The inherent or designed mechanical resiliency of the material of joint 310 is such that ball 78 is able to snap into spherical socket surface 318 and be retained therein. Similarly, frustoconical surface 312 is similarly dimensioned to tightly squeeze the conical pin of clamp 100 of FIG. 3 so that in either case, pad 300 connects to and is retained on either arterial clamp 10 or 100 without the need for any other retention mechanism or adjustment of pad 300. The retention is not so tight, however, that pad 300 cannot be easily removed and reapplied as many times as needed.

Rectangular slot 302 is provided with rounded entry points 324 and rounded interior corners 326 to reduce any sharp pressure points. As best shown in FIG. 4, surface 306 of pad 300 is inclined upwardly in portion 328 away from the puncture site as is also depicted in plan view in FIG. 5 so that there is a gentle pressure relief from inside edge 330 of rectangular slot 302 to center 324 of joint 310. Rectangular slot 302 is intended to accommodate the catheter which has been inserted into the femoral compression site. The pressure relief provided by sloping surface 328 reduces the amount of pressure brought to bear against the catheter as it emerges from the puncture site, which is generally displaced immediately below center 324 of pad 300, in order to reduce or prevent tissue trauma which might be caused by an unnecessary hard pressure being placed on the catheter and in turned on the underlying and surrounding tissue. When the catheter is removed, there is still sufficient pressure provided by pad 300 in the immediate radius of the puncture site notwithstanding the gentle relief provided by slope portion 328 to adequately staunch the blood flow from the puncture.

Thus, it may be seen that pad 300 of FIGS. 4 and 5 can be used universally with either arterial clamps 10 or 100 of the design of FIGS. 1 or 3. The loss of engagement contact between spherical socket surface 318 and a conical pin inserted in the cavity 320 does not materially interfere with the ability of pad 300 to be retained on the pin. Further in such instances where the resiliency of the material pad 300 may be such as to create a loss of holding friction, the depth of cavity 320 can be increased so that the same amount of surface is provided for friction engagement in portion 314 of cavity 320. Similarly, the existence of conical surface 312 does not interfere with the operation of the spherical socket surface 318 in upper portion 316 of cavity 320 notwithstanding the loss of most or all of the lower hemisphere of spherical socket surface 318, since the engagement with the azimuthal upper latitude zone is the effective portion of the ball and socket joint that provides retention. The lower portion shown in dotted outline in FIG. 4 which extends through cavity 320 without engagement with any material surface of a ball is largely ineffective to provide engagement even in the prior art design of FIG. 2. The aperture of pad 300 is provided with bevel 322 in a manner which does not in any way interfere with the engagement of cavity 320 with a conical pin.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

I claim:

1. A pad for use in applying pressure to puncture site on a patient adapted for coupling to a clamp of a first and section design comprising:

a disc shaped portion having a peripheral edge, a puncture site contacting side and an opposite side to said puncture site contacting side;

a joint disposed on said opposite side of said disc shaped portion, said joint having a cavity defined therein with a longitudinal axis and a first and second longitudinal section of said cavity, said first section being distal from said puncture site contacting side and said second section being proximate to said puncture site contacting side, the first section of said cavity generally having an internal surface which is an azimuthal section of a spherical surface and thereby forming part of a releasable ball and socket combination permitting coupling to said clamp of said first design and permitting movement of said pad relative to said patient for self-adjustment of said pad and to conform with the contour of said puncture site, said second section of said cavity having an internal frustoconical surface and thereby forming part of a releasable pin and socket combination permitting coupling to said clamp of said second design.

2. The pad of claim 1 further comprising a rectangular slot radially defined within said peripheral edge.

3. The pad of claim 2 wherein said pad has a center, and wherein said rectangular slot has an inner edge defined at a predetermined distance from said center of said pad, said contacting side of said pad being sloped away from said puncture site from the proximity of said center of said pad to said inner edge of said rectangular slot.

4. The pad of claim 2 further comprises a plurality of stiffening ribs extending from said joint outwardly to said periphery.

5. The pad of claim 4 wherein said peripheral edge has rounded smooth contours disposed toward said puncture site.

6. The pad of claim 2 wherein the said second section of said joint has a length of said frustoconical cavity extending to a diameter less than said frustoconical pin to be inserted therein, when said pad is used in said combination with a frustoconical pin of said clamp.

7. The pad of claim 2 wherein said first section of said joint includes a circumferential bevel defined in said first section as an entry aperture to said cavity to permit swiveling of said pad above said joint.

8. The pad of claim 1 wherein said first section of said joint includes a circumferential bevel defined in said first section as an entry aperture to said cavity to permit swiveling of said pad above said joint.

9. The pad of claim 1 wherein said pin of said pin and socket combination is frustoconical in shape and wherein said second section of said joint has a length of said frustoconical cavity extending to a diameter less than said frustoconical pin to be inserted therein.

10. The pad of claim 9 wherein said pin has an engagement surface with a predetermined longitudinal length and wherein said second section of said joint has a longitudinal length which is as long as said predetermined length of said engagement surface of said pin.

11. The pad of claim 1 wherein said azimuthal spherical surface of said cavity is at least that portion of said spherical surface from the equator to an upper latitude.

12. A pad for use in applying pressure to a puncture site of a patient by a clamp comprising:

a pressure plate having a peripheral edge, a contacting surface for applying pressure to said puncture site and a surface opposing said contact surface; and an universal joint adapted to be temporarily coupled to at least two different types of insertion elements, said universal joint fitting either of said at least two insertion elements without any required adjustment of said pad.

13. The pad of claim 12 wherein said universal joint temporarily couples to either an insertion element capable of swiveling or to a fixed insertion element incapable of swiveling.

14. The pad of claim 13 wherein said insertion element capable of swiveling comprises a ball and socket combination.

15. The pad of claim 13 wherein said insertion element not capable of swiveling comprises a forced-fit pin and socket combination.

16. The pad of claim 15 wherein said force-fit pin is a frustoconical shaped pin.

17. The pad of claim 12 further comprising a rectangular slot defined in said pressure plate.

18. The pad of claim 17 wherein said rectangular slot and peripheral edge of said pressure plate are smooth to avoid high pressure points.

19. The pad of claim 12 wherein said universal joint is comprised of rigid material having a predetermined amount of resiliency so that said insertion elements are temporarily coupled to said pad by compression of said universal joint about said insertion element.

20. The pad of claim 19 wherein said universal joint temporarily couples to an insertion element capable of swiveling and a fixed insertion element incapable of swiveling and wherein said insertion element not capable of swiveling comprises a forced-fit pin.

* * * * *

UNITED STATES PATENT AND TRADEMARK OFFICE
CERTIFICATE OF CORRECTION

PATENT NO.   : 6,004,343
DATED        : December 21, 1999
INVENTOR(S)  : Paul A. Kurth Page 1 of 1

It is certified that error appears in the above-identified patent and that said Letters Patent is hereby corrected as shown below:

UNIVERSAL PRESSURE PAD FOR FEMORAL CLAMPS

Inventor: Paul A. Kurth, Rancho Palos Verdes, California

*No Assignee

Appl. No.: 09/165,163

Filed: October 1, 1998

Signed and Sealed this

Twenty-fifth Day of December, 2001

Attest:

Attesting Officer

JAMES E. ROGAN
Director of the United States Patent and Trademark Office